United States Patent
Marzotto et al.

(10) Patent No.: US 12,076,434 B2
(45) Date of Patent: Sep. 3, 2024

(54) METHOD OF PRODUCTION OF A PLANT CELL EXTRACT OF HYDROXYPROLINE RICH GLYCOPROTEINS INCLUDING EXTENSINS

(71) Applicant: Croda Italiana S.P.A, Mortara (IT)

(72) Inventors: Chiara Marzotto, Mortara (IT); Roberto Dal Toso, Mortara (IT)

(73) Assignee: Croda Italiana S.P.A., Mortara (IT)

( * ) Notice: Subject to any disclaimer, the term of this patent is extended or adjusted under 35 U.S.C. 154(b) by 768 days.

(21) Appl. No.: 17/253,423

(22) PCT Filed: Jul. 4, 2019

(86) PCT No.: PCT/EP2019/067943
§ 371 (c)(1),
(2) Date: Dec. 17, 2020

(87) PCT Pub. No.: WO2020/007959
PCT Pub. Date: Jan. 9, 2020

(65) Prior Publication Data
US 2021/0169775 A1    Jun. 10, 2021

(30) Foreign Application Priority Data
Jul. 6, 2018 (IT) .................. 102018000006983

(51) Int. Cl.
*A61K 8/9789* (2017.01)
*A61K 8/64* (2006.01)
*A61K 8/97* (2017.01)
*A61Q 19/08* (2006.01)

(52) U.S. Cl.
CPC .............. *A61K 8/9789* (2017.08); *A61K 8/64* (2013.01); *A61K 8/645* (2013.01); *A61K 8/97* (2013.01); *A61Q 19/08* (2013.01)

(58) Field of Classification Search
CPC .................................. A61K 8/64; A61K 8/645
See application file for complete search history.

(56) References Cited

U.S. PATENT DOCUMENTS

| | | | |
|---|---|---|---|
| 5,443,855 A * | 8/1995 | Wolf ...................... | A61Q 19/00 514/846 |
| 6,072,030 A | 6/2000 | Bombardelli et al. | |
| 2013/0022580 A1 | 1/2013 | Pressi et al. | |

FOREIGN PATENT DOCUMENTS

| | | |
|---|---|---|
| KR | 20070117355 A | 12/2007 |
| WO | 9620284 A1 | 7/1996 |
| WO | 2011124848 A1 | 10/2011 |

OTHER PUBLICATIONS

Miller et al, Production and harvesting of ionically wall-bound extensin from living cell suspension cultures. Plant Cell, Tissue and Organ Culture (1992), vol. 31, No. 1, pp. 61-66 (Year: 1992).*
Heckman et al., "Characterization of Native and Modified Extensin Monomers and Oligomers by Electron Microscopy and Gel Filtration", Plant Physiol., 1988, vol. 86, pp. 848-856.
Kieliszewski et al., "Purification and Partial Characterization of a Hydroxyproline-Rich Glycoprotein in a Graminaceous Monocot, *Zea mays*", Plant Physiol., 1987, vol. 85, pp. 823-827.
Qi, et al., "Solubilization and Partial Characterization of Extensin Fragments from Cell Walls of Cotton Suspension Cultures", Plant Physiol., 1995, vol. 108, pp. 1691-1701.
Showalter et al., "A Bioinformatics Approach to teh Identification, Classification, and Analysis of Hydroxyproline-Rich Glycoproteins", Plant Physiology, 2010, vol. 153, pp. 485-513.
International Search Report and Written Opinion for International Application No. PCT/EP2019/067943, dated Oct. 8, 2019, 10 pages.

* cited by examiner

*Primary Examiner* — Qiuwen Mi
(74) *Attorney, Agent, or Firm* — Buchanan Ingersoll & Rooney PC

(57) ABSTRACT

The method for producing a plant cell extract of hydroxyl rich glycoproteins (HRGP), including extensins, by extraction from plant cell walls (PCW), comprises subjecting a biomass of whole dedifferentiated plant cells to the following treatment: —Breaking the cells for producing a cell homogenate in which the intracellular molecules are solubilized; —Eliminating the solubilized intracellular molecules by washing the cell homogenate with water and diafiltering on a 0.2 μm filter; —Extracting the HRGP from the PCW by adding a salt thereby forming an HRGP enriched salted extract suspension; —Filtering the HRGP enriched salted extract suspension to discard the PCW debris and recover the desired enriched HRGP salted extract. Results on beautifying and on the general state of the skin and of its annexes can be observed with the use of the HRGP extracts according to the invention, in particular: on the texture moisturising capacity is improved; skin is better protected against external aggressions); on the mechanical properties (skin is denser, replumped, firmer, more toned and more elastic); and on the complexion (skin is brighter).

13 Claims, No Drawings
Specification includes a Sequence Listing.

SEQUENCE LISTING

```
<160> NUMBER OF SEQ ID NOS: 4

<210> SEQ ID NO 1
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 1

Lys Thr Thr Lys Ser
1               5

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 2

Gly Gln Pro Arg
1

<210> SEQ ID NO 3
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 3

Val Gly Val Ala Pro Gly
1               5

<210> SEQ ID NO 4
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 4

Lys Thr Phe Lys
1
```

METHOD OF PRODUCTION OF A PLANT CELL EXTRACT OF HYDROXYPROLINE RICH GLYCOPROTEINS INCLUDING EXTENSINS

TECHNICAL FIELD

The present invention relates to a method of extraction of monomeric hydroxyproline rich glycoproteins (HRGP), including extensins, from the plant cell walls of plant cells obtained by in vitro culture. The present invention is also directed to an extract rich in HRGP obtained according to this method, and ingredient, composition, and use thereof in the medical, veterinary, dietary and cosmetic fields.

PRIOR ART

The plant cell wall (PWC) is a complex extracellular structure present in all plant cells. In differentiated tissues, such as stem or leaves, typical of adult plants, the PCW is composed of polysaccharides, lignin and proteins with structural and defensive functions. The polysaccharide fraction of the PCW is mainly composed of cellulose, hemicellulose and pectins, whereas the lignin results from the polymerization of molecular phenols and hydroxycinnamic derivatives secreted from the cells which form intermolecular crosslinks with each other and all macromolecules present.

The major biological function of the PCW is to provide a nutrient permeable, but mechanically rigid and protective, barrier around each plant cell.

PCWs have been distinguished in two different types.

The primary PCWs are typical of young, fast growing plant cells that require protection and mechanical support, but also need to rapidly expand in volume to proliferate. Thus, the primary PCWs, with low lignin content, are continuously remodeled and the addition of new monomeric and polymeric constituents is constant to increase cell surface area.

On the other hand, secondary PCWs, with high lignin content, are typical of mature and differentiated plant cells with fixed volume. These cells have PCWs with highly increased and permanent rigidity, due to the significant levels of crosslinks among the macromolecule constituents.

PCW proteins are functionally important to modify the structure of the PCW during differentiation or following stress, and can be distinguished, according to their interactions with cell wall components.

Proteins which have little or no interactions with cell wall components and thus move freely in the extracellular space (or apoplast) can be found in liquid culture media of cell suspensions or seedlings or can be extracted with low ionic strength buffers.

Other proteins might be weakly bound to the matrix by Van der Waals interactions, hydrogen bonds, hydrophobic or ionic interactions. Such proteins may be extracted by salt solutions and most of them have a basic isoelectric point (pI) ranging from 8 to 11 so that they are positively charged at the acidic pH of cell walls. Negatively charged pectins contain polygalacturonic acid that provides negative charges for interactions with proteins with a high pI. Such interactions would be modulated by extracellular pH and $Ca^{2+}$ concentration, degree of pectin esterification and by mobility and diffusion coefficients of these macromolecules.

Finally, some cell wall proteins can be covalently bound to other PCW components, so that they are still resistant to salt-extraction.

The analysis of the proteins that are structurally present in the plant cell wall has highlighted the role played by the large family of hydroxyproline rich glycoproteins (HRGP) as major components. In the HRGP group further subgroups have been distinguished such as the hydroxyproline rich lectins, the arabinogalactans proteins and extensins.

More specifically, the amino acid sequence of extensins is highly repetitive and contains a characteristic penta-peptide sequence (Ser-Pro-Pro-Pro-Pro) where the proline (Pro) residues are hydroxylated by post-translational like conversion of proline to hydroxyproline (Hyp) by a membrane-bound prolyl 4-hydroxylases (P4Hs) to become a penta-peptide with hydroxyproline (Ser-Hyp-Hyp-Hyp-Hyp). Essentially all Hyp and Serine (Ser) residues of the penta-peptide sequence are then glycosylated and in some cases the glycosylation comes to about 50% of the weight of the molecule. Typically, HRGPs undergo glycosylation by glycosyltransferases. Hyp is glycosylated with 1 to 4 L-arabinose (Araf) residues and Ser is glycosylated with a D-galactose (Gal) residue. Thus L-arabinose is the major carbohydrate component of HRGP. Both the high content of Hyp residues and level of glycosylation confer to HRGPs, and specifically to extensins, a very rigid rod like structure resistant to protease mediated hydrolysis.

As illustrated in Showalter et al., "A Bioinformatics Approach to the Identification, Classification, and Analysis of Hydroxyproline-Rich Glycoproteins", Plant Physiology (2010), 153:485-513, there are various forms of HRGP which differ in the sequence of amino acids that is interposed between two adjacent Ser-(Hyp)$_4$ sequences (corresponding to SPPPP sequences), among which there are lysines that precede the SPPPP sequence, and there are one or more tyrosines following the SPPPP sequence, so that a KSPPPPY sequence is very frequent. It is known that tyrosines (Tyr or Y) are involved in the formation of both intra- and inter-molecular links and basic lysine residues (Lys or K) are important for the ionic interactions with the acidic carboxyl moiety of polygalacturonic and polyglucuronic acids of the PCW.

HRGP are among the major structural proteins and are present in the primary cell wall and contribute significantly to the resistance to pathogenic attack by bacteria, yeast and fungi. It's well known that the extensins are particularly difficult to extract from the cell wall. In fact, HRGP and in particular extensins, are initially synthesized and secreted into the primary PCW as large soluble glycosylated monomers (60 kDa to 90 kDa) while the cells are expanding and proliferating in the meristem tissues and subsequently, during differentiation, or following oxidative and biotic stress, become enzymatically crosslinked by covalent bonds formed between tyrosine residues present on adjacent HRGP monomers but also with polysaccharides and lignin thus becoming insoluble in the PCW through numerous intermolecular bridges. This rigid and insoluble structure, together with polysaccharides such as cellulose, ensures the necessary solidity and mechanical tension to define the shape and volume of the plant cells.

A method to extract HRGP fragments from the differentiated and secondary PCW is disclosed (WO2011/124848), requiring a hydrolytic treatment with various chemical agents to produce a hydrolysate of HRGP consisting of small fragments of glycosylated peptides of various sizes. Following extensive enzymatic hydrolysis, HRGP are extracted from secondary PCWs, essentially as hydrolyzed glycol-peptides, as disclosed in WO2011/124848.

Attempts have also been made to extract HRGP in its monomeric form, by developing young plants (U.S. Pat. No.

5,443,855) to obtain undigested native monomeric HRGP, however no determination of Hyp content was disclosed.

The interest in HRGP for commercial applications derives from their structural similarity to animal collagen due to the high content of proline (Pro) and hydroxyproline (Hyp), ranging between 10% to 50% of the protein molecular mass weight and very similar to the Pro and Hyp determined in human collagen (15% to 20% w/w). In fact, some cosmetic applications report the use of hydrolysates of extensins as "vegetable collagen" (KR20070117355). The molecular weight of the hydrolysates of extensins are among the 0.1 KDa to 1.5 KDa range, while the weight of a monomeric HRGP proteins can be greater than 100 KDa. Both monomeric and hydrolyzed forms of extensins have been proven useful in cosmetic applications as analog of animal collagen to reduce wrinkles and improve skin tone (U.S. Pat. No. 5,443,855).

However, the very low yields and sustainability of the HRGP extraction procedures disclosed above are strong limits to an economically valuable use of HRGP as a substitute for animal collagen.

It has been proposed, as a solution to this problem, to use dedifferentiated and/or meristematic plant cell cultures (PCC) as a source of HRGP. As for other eukaryotic cells, also for PCC there are three main growth phases following inoculum: 1) an initial Lag phase with little or no cell division and biomass growth; 2) a Logarithmic (Log) exponential phase with maximum cell division rate and biomass increase; 3) a Stationary phase where cell number does not increase, but cells may continue to expand in volume thus increasing biomass fresh weight. PCC undergoing exponential growth have mainly primary PCWs, containing all major macromolecular structural components, but with reduced levels of inter- and intra-molecular crosslinks.

Compared to adult plants, PCC provides a fast growing, homogeneous biomass, rich in primary cell walls that can be considered as a renewable, sustainable and potentially economical alternative source of plant metabolites, including proteins such as HRGPs. Indeed several scientific publications (Smith et al., "Isolation of extensin precurors by direct elution of intact tomato cell suspension cultures", Phytochemistry (1984), Vol. 23, No. 6, pp. 1233-1239, Heckman et al., "Characterization of Native and Modified Extensin Monomers and Oligomers by Electron Microscopy and Gel Filtration", Plant Physiol. (1988), 86, 848-856, Ribeiro et al., "The contribution of extensin network formation to rapid, hydrogen peroxide-mediated increases in grapevine callus wall resistance to fungal lytic enzymes", Journal of Experimental Botany (2006), 57: 2025-2035, Brownleader et al., "Investigations into the molecular size and shape of tomato extensin", Biochem. J. (1996), 320, 577-583) and patents (EP0800585) indicate that PCC can undergo salt extraction (such as NaCl, KCl, $CaCl_2$, $AlCl_3$, $LaC_2$,) to obtain monomeric HRGPs ionically bound to the PCW.

To extract monomeric HRGP, an early indication provided by the scientific literature on PCC cells shows that the extraction had to occur with a biomass recovered during the fast-growing logarithmic phase of cells. Smith et al. taught that extraction had to occur between 4-7 days of culture from inoculum for tomato cell line and disclosed that in this period there was a peak of extraction capacity, whereas between 10 to 14 days from inoculum, the extracted HRGP by saline solutions was reduced to approximately 20% of the peak value.

In the same way, Dey et al. ("Extensin from suspension-cultured potato cells: a hydroxyproline-rich glycoprotein, devoid of agglutinin activity", Planta (1997) 202: 179-187) disclosed that HRGP extraction from potato PCC had to be done at 7 days from inoculum, and this same indication was confirmed by other experiments which find HRGP essentially insoluble after 14 days of culture, due to crosslinks with polysaccharides (Qi et al., "Solubilization and Partial Characterization of Extensin Fragments from Cell Walls of Cotton Suspension Cultures, Plant Physiol. (1995), 108: 1691-1701), and thereafter adopted by others authors (WO96/20284, Brownleader et al., "Investigations into the molecular size and shape of tomato extensin", Biochem. (1996) J. 320: 577-583).

According to the prior art (Smith et al. and Qi et al.), after the fast-growing logarithmic phase the level of extractable HRGPs is highly reduced due to crosslinks.

One important limitation in the methods disclosed in the prior art of PCC as a source of HRGP, of extensins in particular, is the low yield of HRGP that are obtained, ranging from 0.7 mg Hyp/g cell dry weight from tomato cell lines (Smith et al.) to 0.092 mg Hyp/g cell dry weight from *Zea mays* cell lines (Kieliszewski et al., "Purification and Partial Characterization of a Hydroxyproline Rich Glycoprotein in a Graminaceous Monocot, *Zea mays*", Plant Physiol. (1987), 85, 823-827).

Thus, a first aim of the present invention is to overcome this drawback of poor yields when using a PCC method, and to provide a new method of production of HRGP, and of extensins in particular, with yields suitable for industrial, and to form products suitable for cosmetic, pharmaceutical, veterinary and dietary applications.

Frequently, the extraction process of HRGP from young plants, or adult differentiated tissues, carries also many proteins from the intracellular cytoplasmic compartment and non-HRGP proteins loosely bound to the PCW, that reduce purity level of the final HRGP preparation. Furthermore, polyphenols which, following oxidation and polymerization are involved in lignin formation, may reduce extraction yield due to crosslinks with secreted HRGP.

Thus, another aim of the present invention is to overcome this drawback by providing a production method that allows obtaining a final extraction product comprising the desired HRGP non-contaminated with intracellular and extracellular proteins, without polyphenols, which can be industrially produced in large volume reactors.

SUMMARY OF THE INVENTION

According to the invention a method for producing a plant cell extract of monomeric hydroxyl rich glycoproteins (HRGP), including extensins, by extraction from plant cell walls (PCW) is provided, the method comprising subjecting a biomass of dedifferentiated and/or meristematic plant cells to the following treatment:

A) Breaking the whole cells to produce a cell homogenate in which the intracellular molecules are solubilized;

B) Recovering the PCW by eliminating the solubilized intracellular molecules by washing the cell homogenate with an aqueous solution;

C) Extracting the HRGP from the PCW by adding a salt thereby forming an HRGP enriched salted extract suspension;

D) Recovering the HRGP enriched salted extract suspension by discarding the PCW debris.

The main difference with the prior art, where the HRGP salt extraction step is to be performed on a biomass comprising whole plant cells, resides in the fact that according to the invention the recovering of the HRGP is done on a homogenized biomass, where the plant cells are broken on purpose and where the intracellular molecules of the cells are released and mixed with the cellular debris such as the PCW comprising the HRGP.

In step A), "whole" cells mean cells that are entire, not broken. In this step, substantially all the whole cells are broken.

According to the invention, a treatment step B) is thereafter specially performed on the cell homogenate to substantially discard the non-desired intracellular molecules that would otherwise contaminate the extract of HRGP.

These method steps allow advantageously to eliminate the non-desired molecules and to offer an industrial processing easier to carry out than handling whole cells with the risk of leakage and breaking.

According to another advantageous aspect, the invention method provides directly a final extract highly enriched in HRGP without the need of further purification treatments.

Furthermore, according to the method of the invention, surprisingly and advantageously the harvesting of the biomass can be performed in the stationary growth phase following the logarithmic phase where the HRGP crosslinking and reticulation can be present. Thanks to the breaking step according to the invention, some PCW crosslinks may be weakened and more HRGP are extracted. This step can be performed by mechanical or chemical lysis, or enzymatic digestion. Preferably the breaking step A) is performed by acidic lysis enhancing the weakening of the PCW. Then to further enhance the weakening of crosslinks within the PCW after acid lysis, the whole cell homogenate obtained in step A) can be incubated for at least 30 min, preferably at least 2 hours, more preferably at least for 6 hours, even more preferably at least 18 hours.

As the harvesting is performed on the stationary phase with a bigger biomass volume, because of a bigger volume and surface of each cell with, thus, a bigger content of PCW, enhanced quantities of HRGP can be advantageously obtained, compatible with an industrial development. Preferably the harvesting is performed after around 12-16-days of culture (or days from inoculum), preferably 14 days; corresponding to an increase of the biomass after the end of the logarithmic proliferation phase of approximately 50% to 90%, preferably 75% to 80%.

Examples are given below to illustrate these results. For example, with an *Ajuga reptans* cell biomass a yield of 73.3% is obtained at 14 days of culture which is much more than the maximum yield disclosed in the prior art.

According to other preferred features, the HRGP extraction step C) is performed by adding inorganics cations, preferably calcium ($Ca^{2+}$), potassium ($K^+$) and sodium ($Na^+$). The addition of salt at step C can be performed by adding either a saline solution or a salt powder.

Still according to preferred features, in step B) of the method of the invention, the eliminating of the solubilized intracellular molecules by washing with an aqueous solution is performed by diafiltering on a 0.2 m filter or by centrifugation. Similarly, according to preferred feature the discarding of the PCW debris in step D) is performed by filtering or centrifugation.

Also, advantageously with the aim of increasing the purity of the extract and preparing the HRGP extract solution to the buffer conditions adequate for enzymatic hydrolysis, an additional step E), performed after step D), of simultaneously de-salting and concentrating the enriched HRGP salted extract by an ultrafiltration using a 10 kDa filter can be performed.

According to the method of the invention, an extract comprising enriched HRGP is obtained after the step D) or the optional step E) having the following profile of HRGP glycoprotein molecules with molecular weight ranging from 16 kDa to 91 kDa with most abundant content of proteins at 31 kDa, 45 kDa and 66 k Da.

This enriched HRGP extract obtained after step D) or optional step E) can be subjected to a further step of hydrolysis for increasing the content of small HRGP fragments, preferably of HRGP fragments <5 kDa. Such hydrolysis is preferably a carbohydrase and protease enzymatic hydrolysis.

The method of the invention can be performed on a biomass of de-differenciated cells of any plant, since any PCW comprises HRGP by nature. Examples are given below on cell biomass of *Buddleja davidii*, *Gardenia jasminoides*, *Ajuga reptans*, *Syringa vulgaris* and *Magnolia grandifolia*, that shown particularly good yields obtained and were never disclosed as a source of HRGP in the prior art.

The invention provides specifically an extract of HRGP from *Buddleja davidii*, *Gardenia jasminoides*, *Ajuga reptans*, *Syringa vulgaris* and *Magnolia grandifolia*, that can be obtained according to the method of the invention and comprising advantageously at least 20% of protein below 5 kDa.

*Buddleja davidii*, commonly known as summer lilac, butterfly-bush or orange eye, is part of the Scrophulariaceae family, native to Sichuan and Hubei provinces in central China and Japan, and widely grown in Europe. *Buddleja davidii* is a vigorous shrub, growing to 5 m in height. The honey-scented, lilac to purple inflorescences are terminal panicles, less than 20 cm long. Flowers are perfect (having both male and female parts), hence are hermaphrodite. *Buddleja davidii* cultivars are much appreciated worldwide as ornamentals and for the value of their flowers as a nectar source for many species of butterfly. Traditional medicinal plants of the *Buddleja* genus are known for their wound healing, anti-inflammatory and anti-bacterial properties.

*Gardenia jasminoides*, commonly known as gardenia, cape jasmine, cape jessamine, danh-danh or jasmin, is part of the Rubiaceae Family, native of China and Asia. *Gardenia jasminoides* is a shrub with greyish bark and dark green shiny evergreen leaves. White flowers bloom in spring and summer and are highly fragrant. They are followed by small oval fruit. *Gardenia jasminoides* is widely used as a garden plant in warm temperate and subtropical gardens. It can be used as a hedge. *Gardenia jasminoides* fructus (fruit) is being used within traditional Chinese medicine to "drain fire" and thereby treat certain febrile conditions.

*Ajuga reptans*, also known as common bugle, blue bugle, bugleherb, bugleweed, carpetweed, and carpet bugleweed, is a perennial plant of the Lamiaceae family, native to Europe, Caucasus and Iran, growing in woods and rough pastures. *Ajuga reptans* is a sprawling perennial herb with erect flowering stems and grows to a height of about 10 to 35 cm. The stems are squarish with hairs on two sides and the plant has runners that spread across the surface of the ground. The purplish-green, stalked leaves are in opposite pairs. The leaf blades are hairless and are elliptical or ovate with a rounded tip and shallowly rounded teeth on the margin. The inflorescence forms a dense raceme and is composed of whorls of blue flowers, each with dark veins on the lower lip. *Ajuga reptans* is traditionally used for ornamentation and for its anti-inflammatory properties, especially to relieve mild rheumatic pain. The herb has been used in traditional Austrian medicine internally as a tea for the treatment of disorders related to the respiratory tract. Bugle is also known as "carpenter's herb" due to its supposed ability to stem bleeding.

*Syringa vulgaris*, known as Lilac or common Lilac, is a perennial deciduous shrub from the Oleaceae family. Originally from South Eastern Europe, it is now a spontaneous plant throughout Europe where it is widely used as an ornamental garden plant. It features ovate or heartshaped leaves with full margins. The small flowers are grouped in fragrant, brightly coloured clusters at the ends of the branches. A green dye is obtained from the flowers and the leaves and a yellow-orange dye is obtained from the twigs. An essential oil is obtained from the flowers and used in perfume fragrances.

*Magnolia grandiflora*, also known as southern *magnolia* or bull bay, is a large and beautiful tree of the family of Magnoliaceae, with pyramidal port, a height being able to reach 30 m. It originates in North America and is largely cultivated as ornamental tree. *Magnolia grandiflora* contains phenolic constituents shown to possess significant antimicrobial activity. Magnolol, honokiol, and 3,5'-diallyl-2'-hydroxy-4-methoxybiphenyl exhibited significant activity against Gram-positive and acid-fast bacteria and fungi. The leaves contain coumarins and sesquiterpene lactones.

The present invention provides also the use of an HRGP extract that can be obtained according to the method of the invention for a non-therapeutic cosmetic treatment or for a medical treatment.

According to other features, the present invention provides:
  a cosmetic, medical, dietary or veterinary ingredient comprising an extract that can be obtained according to the method of the invention and a physiologically acceptable medium,
  a composition adapted for cosmetic, pharmaceutical, dietary or veterinary use, comprising an effective amount of an extract that can be obtained according to the method of the invention, or of the ingredient of the invention, in a physiologically acceptable excipient, and
  veterinary and dietary products comprising said composition.

DETAILED DESCRIPTION OF THE INVENTION

The present invention will be better understood in the light of the following detailed description of examples.

Preparation of Biomass of De-Differentiated Cells of Different Plants

The following cell lines were generated, cultured, stabilized and tested: *Ajuga reptans, Buddleja davidii, Gardenia jasminoides, Syringa vulgaris* and *Magnolia grandiflora*.

Stabilized and selected cell lines derived from these plants (from dedifferentiated and/or meristematic plant cells) were grown on solid culture medium (Gamborg B5 containing 1% (weight/volume=w/v) of Agar, 30 g/L of sucrose, 1 g/L of vegetable peptone, 1 mg/L of naphthalenacetic acid (NAA), 0.2 mg/L of indolacetic acid (IAA) and 1 mg/L of kinetine, final pH of 6.5) and then were inoculated into five Erlenmeyer flasks each of the capacity of 3 liters containing 1000 ml of liquid medium (Gamborg B5 containing 30 g/L sucrose, 1 g/L vegetable peptone, 1 mg/L NAA, 0.2 mg/L IAA and 1 mg/L kinetine, final pH of 6.5). The amount of plant cells inoculated in liquid medium was equal to 5% w/v. The suspensions thus obtained were incubated at 25° C. in the dark and placed over an orbital stirrer set at 120 RPM.

After 14 days of incubation, the vegetable biomass (5 liters of cell suspension) was collected and filtered on nylon mesh with a Buchner filter a pore mesh size of 50 m.

HRGP Extraction Protocol According to the Invention
  Acid lysis: a mineral acid (example $H_3PO_4$ and HCl) or an organic acid (for example acetic acid, lactic acid or citric acid) is added to the cell biomass after 14 days of culture from inoculum (at the end of the stationary growing phase during which the size of the cells grows) to pH 2;
  Incubation of the cell homogenate in acid lysis solution for 18 hours at 4° C.;
  Washing of the cell homogenate with water (by diafiltration on 0.2 m filter), in order to remove all soluble intracellular molecules and obtain a fraction enriched in PCWs (=PCW fraction);
  Salt solution extraction: 200 mM $CaCl_2$ and L ascorbic acid (1 g/L) are added directly to the PCW fraction and the suspension is stirred 10 minutes at 4° C.;
  Recovering of the HRGP: The HRGP enriched solution is separated from the exhausted PCW by a filtration on any suitable filtration device and collected for further processing; the remaining PCW is discarded; the calcium rich HRGP solution is de-salted and concentrated at the desired concentration of Hyp by an ultrafiltration on a 10 kDa membrane; the final buffer of the HRGP extract being citrate buffer, 0.05M, at pH 4.

Following ultrafiltration with the 10 kDa membrane, the retentate solution, which constitutes the HRGP extract, is lyophilized.

For Comparison, HRGP Extraction Protocol of the Same Culture Used Previously According to the Prior Art (on Whole Cells):
  Cells are harvested by filtration at 6-10 days from inoculum (in the fast-growing logarithmic phase where the number of cells grows) with a Buchner filter, at 50 m;
  The extraction buffer (200 mM $CaCl_2$+1 gr/L ascorbic acid at pH 3) is added to the cells at the concentration of 200 mg cells/ml buffer and the cell suspension is stirred for 10 minutes at 4° C.;
  The extract is then collected after filtration with a Buchner filter (50 m) and the whole cells (not broken) are discarded;
  The calcium rich HRGP solution is de-salted and concentrated at the desired concentration of Hyp by an ultrafiltration on a 10 kDa membrane. The final buffer of the HRGP extract is citrate buffer, 0.05M, at pH4;

The content of HRGP is measured by utilizing the high acid and high temperature hydrolysis of all the macromolecular PCW components and subsequent determination of the hydroxyproline (Hyp) content, according to Kivirikko et al. "A colorimetric method for determination of hydroxyproline in tissue hydrolysates", Scand J Clin and Lab. Investigations 128-133, 11, 1959.

This procedure consists of two subsequent steps the first to hydrolyze the sample and the second to measure hydroxyproline. To hydrolysis, 1 mL of liquid sample was transferred into a hydrolysis tubes and taken to dryness with nitrogen gas in the evaporator. Subsequently 6M HCl were added to the dried samples, at the same volume (1 ml sample/l ml acid); Solid dry samples (50 mg) were added directly to 1 mL of 6M HCl. All samples were incubated 15-18 h at 110° C. After the hydrolysis, the samples were taken to dryness with nitrogen gas.

To determine hydroxyproline content the samples were re-suspended with acetate/citrate buffer at the same volume of HCl 6M, used in the hydrolysis. A standard curve with hydroxyproline was prepared in 1.5 ml test tubes, with acetate/citrate buffer, at concentrations: from 0 μg/mL to 10 μg/mL. In another 1.5 ml test tube, were mixed 100 μL of sample (or standard) and 100 μL 7% Chloramine T solution and incubated 25 minutes at room temperature in the dark. 100 μL Ehrlich's solution were added and the sample incubated for 15 minutes at 60° C. in the dark. 300 μL of each sample were transferred in a 96 well plate and read at a multilabel counter at 540-560 nm. The amount of hydroxyproline (Hyp) was extrapolated from the standard curve, as μg hyp/ml buffer.

Results

The Following table 1 gives comparative results to illustrate the invention of the Hyp content and recovery percentage from the whole cell by salt extraction, alone or after acid lysis at 6 days, 10 days and 14 days of culture.

TABLE 1

|  |  | Days in culture | | | | | | % of |
|---|---|---|---|---|---|---|---|---|
|  |  | 6 | 10 | 14 | 6 | 10 | 14 | increase |
|  |  | Hyp μg/g cell DW | | | % Recovery | | | at 14 days |
| *Buddleja davidii* | Total | 1937.0 | 2322.0 | 2454.0 | 100.0 | 100.0 | 100.0 |  |
|  | Salt extraction | 1518.0 | 1635.0 | 1247.0 | 78.4 | 70.4 | 50.8 |  |
|  | Acid lysis + salt extraction | 1492.0 | 1596.0 | 1655.0 | 77.0 | 68.7 | 67.4 | +33% |
| *Gardenia jasminoides* | Total | 1981.0 | 2164.0 | 2326.0 | 100.0 | 100.0 | 100.0 |  |
|  | Salt extraction | 1539.0 | 1551.0 | 1247.0 | 77.7 | 71.7 | 53.6 |  |
|  | Acid lysis + salt extraction | 1507.0 | 1597.0 | 1606.0 | 76.1 | 73.8 | 69.0 | +29% |
| *Ajuga reptans* | Total | 1933.0 | 2086.0 | 2157.0 | 100.0 | 100.0 | 100.0 |  |
|  | Salt extraction | 1323.0 | 1367.0 | 1118.0 | 68.4 | 65.5 | 51.8 |  |
|  | Acid lysis + salt extraction | 1294.0 | 1401.0 | 1582.0 | 66.9 | 67.2 | 73.3 | +42% |
| *Syringa vulgaris* | Total | 1217.0 | 1358.0 | 1428.0 | 100.0 | 100.0 | 100.0 |  |
|  | Salt extraction | 847.0 | 782.0 | 658.0 | 69.6 | 57.6 | 46.1 |  |
|  | Acid lysis + salt extraction | 822.0 | 857.0 | 934.0 | 67.5 | 63.1 | 65.4 | +42% |

What is observed from the table is that:

The total of Hyp increases from 6 to 14 days. This is inline with the growing size of the biomass.

The percentage of recovery of HRGP decreases from 6 to 14 days with the method of the prior art (salt extraction only, no breaking of the cells). This corresponds to what is disclosed in the prior art, i.e. that the extraction of HRGP is getting more difficult when the HRGP are reticulated in PCW.

The percentage of recovery of HRGP remains substantially the same from 6 to 14 days with the method of the invention (breaking of cells+salt extraction).

At 6 days, the percentage of sedimented whole cell fresh weight is about 20-30%, at 10 days the percentage is about 40-55% and at 14 days about 55-87%. The percentage of Cell Fresh weight (FW) volume was determined by stopping the agitation of cell in the reactor and measuring, after 30 minutes, the percent volume of the cell sediment to the total volume of culture suspension with a specific weight or density for FW of approximately 1 kg/L. For plant cells specific cell density is typically 1.04 kg/L The results show that the method of the invention is much more interesting: for example, for *Ajuga reptans* and *Syringa vulgaris* it allows to increase at 14 days the amount of HRGP of 42% compared to the prior art method.

The following table 2 shows the composition of the lyophilized PCW extract obtained from *Ajuga reptans* and *Gardenia jasminoides* by salt extraction after acid lysis treatment

TABLE 2

| Component | *Ajuga reptans* (% of Extract DW) | *Gardenia jasminoides* (% of Extract DW) |
|---|---|---|
| Carbohydrates | 22.26 | 25.04 |
| Arabinose | 11.15 | 12.3 |
| Galactose | 8.44 | 9.8 |
| Glucose | 1.65 | 0.82 |
| Xylose | 1.02 | 2.12 |
| Proteins | 23 | 8 |
| Hyp | 3.63 | 1.52 |
| Salts | 22.04 | 35.92 |
| Insoluble and unidentified | 32.36 | 31.04 |

The extraction and lyophilization process provides a final extract which corresponds for *Ajuga reptans* to a16.8-fold increase of Hyp content of the extract compared to the cell dry weight content and a6.5-fold increase for the *Gardenia jasminoides* extract.

Furthermore, an amino-acid sequence analysis was made on the *Ajuga reptans* and *Gardenia jasminoides* samples following an additional protein precipitation step with trichloracetic acid to further increase HRGP purity. The samples were analyzed by HPLC-MS/MS evaluation following trypsin digestion and several peptides were identified as HRGP fragments. Specifically, in *Ajuga reptans*, a peptide present in the extracted sample is identical to the leucine-rich repeat extensin-like protein 1 of *Solanum lycopersicum* (accession gi|460408850) in which proline is 19,800 of the total mass in the amino-acid sequence. In the *Gardenia jasminoides* sample, five different peptides (accession: gi|559237 with Pro at 21.2% of mass; gi|1486263 with Pro at 39.500 of mass; gi|460413353 with Pro at 28.000 of mass; gi|460400459 with Pro at 10.700 of mass and gi|460406916 with Pro at 19.800 of mass) were identified as HRGP.

From Table 2, in *Ajuga reptans*, the salt extraction after acid lysis procedure followed by lyophilization yields 36.3 mg of Hyp and 230 mg of proteins per gram of extract dry weight (EDW). This allows to calculate that up to 157.8 mg Hyp/g of proteins in the final extract dry weight are obtained by this procedure. Together with the indication that, in *Ajuga reptans*, Hyp mass content is 19.8% of the total amino-acid sequence mass of the identified HRGP, one can calculate HRGP to be at least 79.7% of the extracted proteins present in the sample. An analogous evaluation for the *Gardenia jasminoides* extracts provides a similar enrichment level.

Furthermore, the arabinose mass content is more than 3 times the mass of Hyp and more abundant than galactose which is in line with the general structure known for HRGPs.

Also, WO 2011/124848 teaches that HRGP can be extracted by enzymatic hydrolysis from soy plant fibers, but the quality and amount are quite different compared to the composition of the extract obtained in the present invention. The amount of Hyp obtained by the method of WO 2011/124848 in the final extract dry weight ranges from 18 mg Hyp/g proteins to a maximum of 30 mg Hyp/g protein.

A gel permeation profile on a HPLC device together with an SDS-PAGE gel electrophoresis were utilized to define the molecular weight profile of the major proteins present in the *Ajuga reptans* HRGP extract in whole cells and after acid lysis and no major difference was detected. In the initial undigested extract with mainly monomeric glycoproteins more that 76% of the measured protein average mass was higher than 5 kDa and 24% was below 5 kDa average peptide mass.

Hydrolysis of the Monomeric HRGP Obtained According to the Invention

Hydrolysed HRGP peptides can be prepared by use of proteases after de-glycosilation. The removal of glycosidic branches form of the monomeric HRGP protein can be obtained by treatment with fluoridric acid (HF) (Mort A J, Lamport D T A. "Anhydrous hydrogen fluoride deglycosylates glycoproteins. Anal Biochem. 1977; 82:289-309"). De-glycosylation of HRGPs is required to allow access of proteases, such as trypsin, to the protein peptide bound backbone to obtain smaller size peptide fragments by enzymatic hydrolysis. Furthermore, WO 2011/124848 teaches how to utilize a sequence or combination of carbohydrases and proteases to extract HRGP peptides from soy fibers and were applied here. A sequence of carbohydrase and proteases was utilized to reduce the peptide size of the HRGP extracts from PCC of *Ajuga reptans*.

Following carbohydrase and protease enzymatic hydrolysis the total amount of detected peptides with average mass below 5 kDa increased from 24% to 57.2% and the fraction of peptides with average mass above 5 kDa was reduced from 76% to 43%. Similar results were obtained for the HRGP extracts from *Gardenia jasminoides, Buddleja davidii* and *Magnolia grandiflora*.

Both the undigested monomeric HRGP extract and the enzymatically hydrolyzed extracts from plants are suitable to be utilized for pharmaceutical, nutritional, veterinary and cosmetic applications.

In vitro evaluations of the action of an extract of HRGPs of the invention are given below, conducted on a *Gardenia* extract of table 2.

1) Improvement of the Dermis and the Dermis/Epidermis Junction (DEJ)

a. Evaluation by Immunofluorescence (IMF): Collagen I Synthesis

The loss of density and thickness of the dermis are related to a reduction of synthesis of macromolecules during aging (intrinsic or extrinsic) by dermal fibroblasts, the cells in charge of their synthesis. Collagen I is the most abundant protein in the dermis.

Protocol

Normal human fibroblasts (NHF) are cultured in 24-well plates for 24 hours. The cells are placed in contact with test products (or their excipient as control) for 6 days. The collagen I produced by the cells is then quantified by fluorescence immunocytology (n=3) on the fixed mats and quantified by image analysis, the results being expressed in arbitrary fluorescence units. Each result is related to the number of cells assessed using the method Hoescht 33258, which marks the DNA. Value obtained for the extract according to the invention is compared with that obtained for the product solvent (control). A study of the variances and a Student's t-test for paired series were performed to judge the significance of the results.

Results

TABLE 3

| Variation of collagen I synthesis by NHF in the presence of the extract according to the invention (IMF method) | |
|---|---|
| Concentrations | % change/control; significance (Student test) |
| Control | Reference |
| 80 ppm | +98.2; p < 0.01 |

No toxic effect was observed.

b. Evaluations by ELISA: Synthesis of Macromolecules of the Dermis and the DEJ

Elastin is synthesized and secreted in the extracellular dermal space. It is the major component, up to 90%, of the elastic fibers.

Fibronectin is a glycoprotein present in the extracellular matrix, which plays a key role in cell adhesion to the extracellular matrix. It can simultaneously bind to the cell and to other extracellular matrix molecules, such as collagen or another fibronectin molecule. To this aim, the fibronectin molecules assemble to form adhesive elastic fibers on the surface of many cells. This determines the mechanical properties (elasticity, suppleness and firmness) of the skin.

Collagen IV forms a two-dimensional network and is one of the major components of the DEJ. Laminins are also contained in the basal layer and participate in the anchoring of cell surfaces to the basal lamina.

The increase of collagen IV and laminin synthesis helps to strengthen/restore the DEJ and thus the flexibility of the whole system dermis/epidermis.

Hyaluronic acid exhibits water-binding and water-attracting attributes, and fills up the spaces between the connective fibers collagen and elastin in the dermis. The increase of hyaluronic acid helps to strengthen/restore the density of dermis.

Protocol

Confluent normal human fibroblasts (NHF) in culture are brought into contact with the extract of the invention to be tested or their excipient (negative control) for 72 hours. After the contact, the culture supernatants are recovered, and the quantity of dermal macromolecules synthesized are assayed by ELISA. Each result is related to the number of cells assessed using the method Hoescht 33258, which marks the DNA. Value obtained for the extract according to the invention is compared with that obtained for the product solvent (control). A study of the variances and a Student's t-test for paired series were performed to judge the significance of the results.

TABLE 4

| | Elastin | Fibronectin | Collagen IV | Laminins | Hyaluronic acid |
|---|---|---|---|---|---|
| results | | | | | |
| Concentrations | 100 ppm | 80 ppm | 100 ppm | 80 ppm | 100 ppm |
| % Change/control; | +94%; | +73%; | +140%; | +114%; | +51%; |
| Significance (Student test) | p < 0.01 | p < 0.01 | p < 0.01 | p < 0.01 | p < 0.05 |

No toxic effects were observed.

These data indicate the potential of the extract according to the invention to prevent and restore the mechanical properties of the skin: density, firmness, suppleness and elasticity. The skin is densified and volumized.

Cosmetic treatments linked to the loss of elasticity, thickness, firmness, density and/or volume of the skin can be envisaged, or to prevent such losses, more particularly treatments of wrinkles and fine lines, of skin sagging.

Medical treatments indicated to repair extracellular matrix of tissues can also be envisaged.

2) Improvement of the Epidermis

Hyaluronic acid is also an important element in the epidermis where it participates to its good hydration. Synthesized and secreted by keratinocytes, it acts in the epidermis like a real sponge, attracting and retaining up to 1000 times its weight in water.

Laminin 5 is important at the level of DEJ. It ensures the proper anchoring of basal keratinocytes on the basement membrane and is responsible for the suppleness of the epidermis. In addition, it stimulates the proliferation of keratinocytes, allowing them to engage in differentiation. On older cells Laminin 5 is no longer replaced as efficiently as on young cells, hence stimulating its biosynthesis the interest of for a better renewal of keratinocytes.

Protocol

Confluent keratinocytes in culture are brought into contact with the products to be tested or their excipient (negative control) for 72 hours. After the contact, the culture supernatants are recovered, and the quantity of laminins and hyaluronic acid synthesized are assayed. Each result is related to the number of cells assessed using the method Hoescht 33258, which marks the DNA. Value obtained for the extracts according to the invention is compared with that obtained for the product solvent (control). A study of the variances and a Student's t-test for paired series were performed to judge the significance of the results.

TABLE 5

| | Hyaluronic acid | Laminins 5 |
|---|---|---|
| results | | |
| Concentrations | 160 ppm | 80 ppm |
| % Change/control; | +59%; | +71%; |
| Significance (Student test) | p < 0.05 | p < 0.01 |

Improvement of the Quality of the Differentiation of Keratinocytes

Near-confluent human keratinocytes are contacted 2, 3 and 6 days with the extract according to the invention (or its placebo) in a suitable culture medium in order to study their phenotypic modifications under the microscope considering the appearance of the cells. With the extract according to the invention (at 200 ppm), results show a clear acceleration of the characteristic phenotypes of the differentiation with presence of structures typical of the upper layers of the epidermis (presence of branched structures characteristic of the rigid proteolipidic) and multilayer appearance of the horny envelope, (refractive network).

The following tables show complementary results on tests performed with the same protocols on extracts of *Buddleja davidii*, *Syringa vulgaris* and *Ajuga reptans* extracts (obtained according to the method of the present invention and similarly to the *Gardenia jasminoides* extract used for the in-vitro presented tests).

TABLE 6

*Buddleja davidii* extract comprising 150 ppm of extensins

| | Hyaluronic acid (ELISA on keratinocytes) | Elastine (IMF on fibroblasts) |
|---|---|---|
| % Change/control | +83% | +202% |

TABLE 7

*Syringa vulgaris* extract comprising 150 ppm of extensins

| | Hyaluronic acid (ELISA on keratinocytes) | Laminins 5 (ELISA on keratinocytes) |
|---|---|---|
| % Change/control | +209% | +69% |

TABLE 8

*Ajuga reptans* extract comprising 150 ppm of extensins

| | Hyaluronic acid (ELISA on keratinocytes) | Laminins 5 (ELISA on keratinocytes) | Collagen 7 (ELISA on keratinocytes) |
|---|---|---|---|
| % Change/control | +47% | +61% | +46% |

All these results show that an extract according to the invention has a beneficial effect on the epidermis, via a better differentiation of keratinocytes, a better hydration and suppleness. The barrier function of the epidermis against exterior aggressions is improved. Skin complexion is embellished.

Prevention Activity on Protein Glycation

In this in tubo model, a Bovine Serum Albumin (BSA) is used as target protein of reducing sugars which create glycated end products; this method allows screening of antiglycation products. Indeed, non-enzymatic glycation between BSA and a reducing sugar (fructose or glucose) is a spontaneous and slow reaction, that can be accelerated by temperature. Advanced glycation end-products (AGEs) on BSA have a natural fluorescence that can be measured at 350 nm/460 nm and ex./em. A decrease of the AGEs observed means an inhibition of glycation. Aminoguanidine is used as a positive control of glycation inhibition.

TABLE 9

Anti-glycation: results on extracts obtained according to the method of the invention

| | | |
|---|---|---|
| Gardenia jasminoides extract | 60 ppm | → −21 |
| | 100 ppm | → −23 |
| | 150 ppm | → −28 |
| Buddleja davidii extract | 60 ppm | → −85 |
| | 100 ppm | → −88 |
| | 150 ppm | → −90 |
| Syringa vulgaris extract | 60 ppm | → −89 |
| | 100 ppm | → −92 |
| | 150 ppm | → −93 |
| Ajuga reptans extract | 60 ppm | → −47 |
| | 100 ppm | → −68 |
| | 150 ppm | → −79 |

A dose dependently activity on AGEs products is observed with all the extracts.

As a result, skin is prevented from fatigue, from the formation of dark circles and under eye bags and from the loss of suppleness of the skin.

Therefore, the invention provides the use of the extract of HRGP to improve the general state of the skin including the scalp and its annexes (such as nails, hair, eyelashes, eyebrows), in particular:
  to prevent and/or treat the intrinsic and extrinsic signs of skin aging: wrinkles, fine lines, discontinuities and roughness of the skin, skin sagging, and/or
  to improve the mechanical properties of the skin, tonicity and/or firmness and/or elasticity of the skin; and/or
  to improve the density of the dermis and epidermis, to give or restore volume to the dermis and epidermis; and/or
  to prevent and/or treat skin dehydration; and/or
  to prevent the skin from protein glycation; and/or
  to prevent cutaneous fatigue; and/or
  to prevent dark circles and under eye bags; and/or
  to prevent loss of suppleness of the skin; and/or
  to improve the brightness of complexion; and/or
  to improve the growth and strength of nails, the regeneration of damaged nails, the hydration of nails accompanied by a decrease of ribs; and/or
  to improve strength and growth of hair.

Results on beautifying and on the general state of the skin and of its annexes can be observed with the use of the HRGP extracts according to the invention, in particular:
  on the texture: the moisturising capacity of the skin is improved; the skin is less rough and softer and skin water loss is reduced; the skin is better protected against external aggressions;
  on the mechanical properties: the skin is denser, replumped, firmer, more toned and therefore more elastic; the extract has a volume-producing, replumping effect;
  on the complexion: the skin is brighter.

In a composition according to the invention the plant extract(s) comprising extensins may be formulated with additional cosmetic active ingredients, optionally supporting and/or complementing the activity, either in the ingredient form, or at the time of producing the final cosmetic composition for the consumer.

This composition may be applied to the face, body, neckline, scalp, hair, eyelashes, body hairs, in any form or vehicles known to those skilled in the art, especially in the form of solution, dispersion, emulsion, paste or powder, individually or premixed or conveyed individually or as a pre-mix, in vectors such as macro-, micro- or nano-capsules, macro-, micro- or, nano-spheres, liposomes, oleosomes or chylomicrons, macro-, micro-, or nanoparticles or macro-, micro- or nano-sponges, micro- or nano-emulsions or adsorbed on organic polymer powders, talcs, bentonites, spores or exines, and other inorganic or organic supports.

In cosmetics, applications may be proposed in the skin-care ranges of the face, body, hair and body hairs and makeup-care ranges.

These ingredients can be of any category depending on their function(s), the place of application (body, face, neck, bust, hands, hair, eyelashes, eyebrows, body hairs, nails, etc.), the desired end effect and the targeted consumer, for example antioxidant, tensor, moisturizer, nourishing, protective, smoothing, remodeling, volumizing (lipofiling), acting on the radiance of the complexion, against undereye bags and dark circles, antiaging, antiwrinkles, slimming, soothing, myo-relaxing, anti-redness, anti-stretch marks, sunscreen, etc. incorporated in or absorbed in or adsorbed on macro-, micro-, and nanoparticles, or macro-, micro-, and nano-capsules, for the treatment of textiles, natural or synthetic fibres, wools, and any materials that may be used for clothing or underwear for day or night intended to come into contact with the skin, handkerchiefs or cloths, to exert their cosmetic effect via this skin/textile contact and to allow continuous topical delivery.

The effective amount depends on various factors, such as the age, the condition of the patient, the seriousness of the disorder or pathology, the administration mode, etc. An effective amount means a non-toxic amount enough to achieve the desired effect.

For example, for a cosmetic treatment of the face, the European Cosmetics Directive has set a standard amount for applying a cream of 2.72 mg/cm$^2$/day/person and for a body lotion of 0.5 mg/cm$^2$/day/person.

In general, the extract(s) according to the invention may be used in any form, in a form bound to or The CTFA ("International Cosmetic Ingredient Dictionary & Handbook" (18th Edition, 2018) published by "The Cosmetic, Toiletry, and Fragrance Association, Inc.", Washington, D.C.) describes a wide variety, without limitation, of cosmetic ingredients usually used in the skincare and scalp care industry, which are suitable for use as additional ingredients in the compositions of the present invention.

At least one of the compounds chosen from vitamin B3 compounds, compounds such as niacinamide or tocopherol, retinoid compounds such as retinol, hexamidine, α-lipoic acid, resveratrol or DHEA, hyaluronic acid, peptides, especially the VW, such as under the trade name Eyeliss™, the N-acetyl-Tyr-Arg-O-hexadecyl, such as under the trade name Idealift™, the Pal-VGVAPG (SEQ ID NO: 1), such as under the trade name Dermaxyl™, the Pal-KTTKS (SEQ ID NO: 2), such as under the trade name Matrixyl®, the Pal-GHK, such as under the trade names Maxi-Lip™ or Biopeptide CL™, the Pal-KMO2K, such as under the trade name Matrixyl® Synthe'6, the Pal-GQPR (SEQ ID NO: 3), such as under the trade name Rigin™, or Matrixyl®3000 in combination with the Pal-GHK, the Pal-K(P)HG, such as under the trade name Matrixyl® Morphomics, or the Pal-KTFK (SEQ ID NO:4), such as under the trade name Crystalide™, cyclopeptides, such as under the trade name Poretect™, can be mentioned, which are active ingredients widely used in cosmetic or dermatological compositions.

Other additional skin care actives that are particularly useful can be found in Sederma's commercial literature and at www.sederma.com or www.crodarom.fr, such as ingredients based on plant extracts (obtained by extraction methods on part(s) of the plant, or by in vitro plant cell culture), or such as biotechnological extracts from microorganism cultures.

The invention claimed is:

1. A method for producing a plant cell extract of monomeric hydroxyl rich glycoproteins (HRGP) by extraction from plant cell walls (PCW), the method comprising subjecting a biomass of dedifferentiated and/or meristematic plant cells prepared by in-vitro cell culture to the following treatment:
   A) breaking whole cells for producing a cell homogenate in which the intracellular molecules are solubilized;
   B) recovering the PCW by eliminating the solubilized intracellular molecules by washing the cell homogenate with an aqueous solution;
   C) extracting the HRGP from the PCW by adding a salt thereby forming an HRGP enriched salted extract suspension; and
   D) recovering the HRGP enriched salted extract suspension by discarding the PCW debris,
   wherein the HRGP include extensins.

2. The method according to claim 1, wherein the step A) is performed by using a chemical lysis, mechanical lysis or enzymatic digestion.

3. The method according to claim 1, wherein in step B) the eliminating of the solubilized intracellular molecules by washing with an aqueous solution is performed by diafiltering on a 0.2 µm filter or by centrifugation.

4. The method according to claim 1, wherein the discarding of the PCW debris in step D) is performed by filtering or centrifugation.

5. The method according to claim 1, comprising an additional step E) after step D) of simultaneously de-salting and concentrating the enriched HRGP salted extract by an ultrafiltration using a 10 kDa filter.

6. The method according to claim 1, wherein the biomass is harvested during stationary growth stage of the biomass where the number of cells is constant, and the size of the cells grows.

7. The method according to claim 6, wherein the biomass is harvested after about 12-16 days of culture, corresponding to an increase of the biomass after the end of proliferation phase of 50% to 90%.

8. The method according to claim 2, wherein, the step A) is performed by chemical lysis and the cell homogenate obtained in step A) is incubated for at least 30 minutes.

9. The method according to claim 8, wherein the step A) is performed by acidic lysis and the cell homogenate is incubated in the acidic lysis solution.

10. The method according to claim 1, wherein the extraction step C) is performed by adding inorganic cations.

11. The method according to claim 5, wherein the enriched HRGP extract obtained after steps E) is subjected to a further step of hydrolysis for increasing the content of HRGP of kDa<5.

12. The method according to claim 11, wherein the hydrolysis is a carbohydrase and protease enzymatic hydrolysis.

13. The method according to claim 1, wherein the biomass of meristematic or dedifferentiated plant cells is prepared by culturing a selected cell line in an appropriate culture medium under culture conditions in a reactor.

* * * * *